United States Patent [19]

Heyn et al.

[11] Patent Number: 4,978,570

[45] Date of Patent: Dec. 18, 1990

[54] GARMENT WITH FOAM CUSHION ELASTIC CLOSURE

[75] Inventors: Hans E. Heyn, North Barrington, Ill.; Russell H. Narramore, Humble, Tex.

[73] Assignee: Exxon Chemical Patents Inc., Linden, N.J.

[21] Appl. No.: 203,394

[22] Filed: Jun. 6, 1988

[51] Int. Cl.$^5$ .................. D03D 3/00; A61F 13/16
[52] U.S. Cl. .................... 428/231; 604/369; 604/385.2
[58] Field of Search ............ 604/358, 369, 385.1, 604/385.2; 428/230, 231; 2/221, 111

[56] References Cited

U.S. PATENT DOCUMENTS

| | | | |
|---|---|---|---|
| 3,860,003 | 1/1975 | Buell | 604/385.2 |
| 4,253,461 | 3/1981 | Strickland et al. | 604/389 |
| 4,352,355 | 10/1982 | Mesek et al. | 604/385.2 |
| 4,402,688 | 9/1983 | Julemont | 604/385.2 |
| 4,425,127 | 1/1984 | Suzuki et al. | 604/366 |
| 4,425,129 | 1/1984 | Karami | 604/385.2 |
| 4,450,026 | 5/1984 | Pieniak et al. | 604/385.2 |
| 4,527,989 | 7/1985 | Karami | 604/385.2 |
| 4,534,769 | 8/1985 | DeJonckheere et al. | 604/369 |
| 4,585,447 | 4/1986 | Karami | 604/385.2 |
| 4,639,949 | 2/1987 | Ales et al. | 604/385.2 |
| 4,640,859 | 2/1987 | Hansen et al. | 604/385.2 |
| 4,657,539 | 4/1987 | Hasse | 604/385.2 |
| 4,681,580 | 7/1987 | Reising et al. | 604/385.2 |
| 4,775,375 | 10/1988 | Aledo | 604/385.2 |
| 4,808,252 | 2/1989 | Lash | 604/385.2 |

FOREIGN PATENT DOCUMENTS 2101468 1/1983 United Kingdom ............ 604/385.1

Primary Examiner—C. Fred Rosenbaum
Assistant Examiner—Sharon Rose
Attorney, Agent, or Firm—M. E. Wilson

[57] ABSTRACT

A disposable diaper having an elastic waist is provided with a foam strip to cushion stresses of the elastic band in the waist area.

3 Claims, 2 Drawing Sheets

GARMENT WITH FOAM CUSHION ELASTIC CLOSURE

BACKGROUND OF THE INVENTION

This invention relates generally to garments with stretchable closures. In one aspect, it relates to a diaper having foam cushion in the elastic waist band.

Although disposable diapers have been in existence for a number of years, it has only recently become popular to employ elastic waist bands on the diaper to secure better body fit. See for example European Publication Nos. 0119815 and 0119827 and U.S. Pat. Nos. 4,714,735 and 4,534,769. The elastic waist band is achieved by securing an elastomeric strip between two inelastic plastic panel members (e.g. backsheet and nonwoven cover sheet) in the waist area. Upon contraction of the elastomeric strip, the inelastic panel members gather in the waist area. The gathering of the inelastic backsheet and the elasticity of the elastomer strip imparts stretchability to the diaper waist. Although the elastic waist band provides for an improved fit, it can also create discomfort because of the stress imposed on the body.

SUMMARY OF THE INVENTION

The present invention provides for an improved elastic garment by incorporating into the elastic area of the garment a foam strip for cushioning the elastic stress. Although the composite structure contemplated by the present invention can be used in a variety of garments, its preferred application is in disposable diapers (including incontinent products) which include an inelastic backsheet, absorbent material, and an inner cover sheet (nonwoven stock). The diaper of the present invention has formed in the waist area an encasement or sleeve (herein referred to as "waist sleeve") which can be integral with the diaper backsheet and/or the inner cover sheet and extend substantially the entire length of the diaper waist. An elastomeric strip is mounted in the waist sleeve and is bonded to an inner wall portion thereof at a plurability of longitudinally spaced locations. The waist sleeve gathers between the bond locations with the elastomeric strip in the contracted position and straightens with the elastomeric strip in the stretched position. Also mounted in the waist sleeve and in overlaying relationship to the elastomeric strip is an elongate cushion or foam strip, preferably made of plastic foam.

A central portion of the plastic foam strip within the waist sleeve is bonded to the elastomeric strip but the outer ends thereof are unsecured. The waist sleeve and the elastomer strip on either side of the bond location of the foam strip is free to move outwardly and inwardly with respect to the foam strip. The foam strip has a length slightly shorter than the length of the waist sleeve in the contracted position of the diaper waist.

When applied to diapers, it is preferred that the elastomeric strip is made of a heat shrinkable thermoelastic, that the diaper back sheet is made of water impermeable plastic film and that the inner sheet is made of a nonwoven plastic.

DESCRIPTION OF THE PREFERRED EMBODIMENTS

Figure 3:
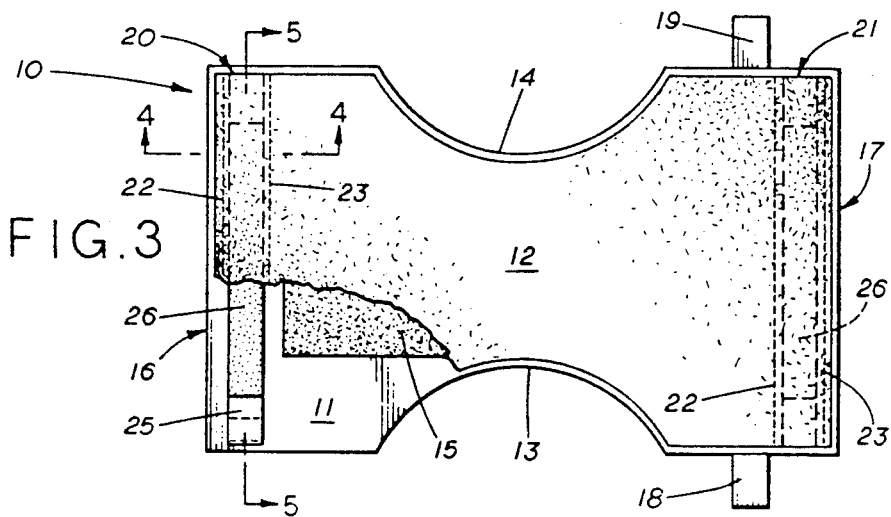
Figure 4:
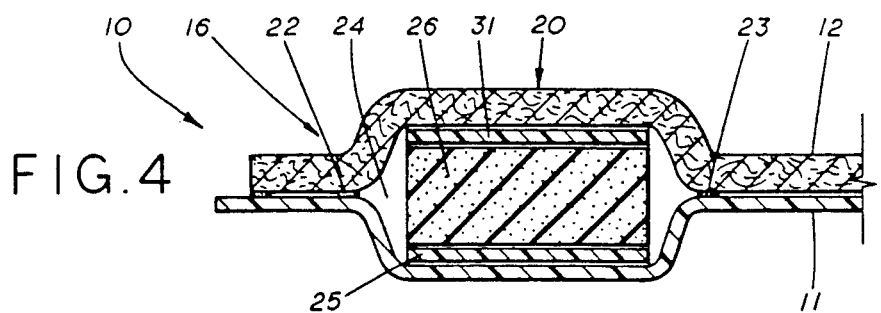
FIG. 4 is a transverse cross sectional view of the diaper waist band taken along the cutting plane 4—4 of FIG. 3.

As shown in FIGS. 3 and 4, a diaper 10 constructed according to the present invention comprises an outer plastic backsheet 11 and an inner cover sheet 12. (The term "sheet" as used herein includes film.) Sheets 11 and 12 are generally square or rectangular in shape and have leg cut outs 13 and 14. An absorbent sheet material 15 is adapted to fit between sheets 11 and 12 forming the diaper. Outer end sections 16 and 17 of the overlapped sheets 11 and 12, when extended around the body and attached by tabs 18 and 19, define the diaper waist section around the body. Tabs 18 and 19 may be of conventional material (e.g. polyolefin tape) and are secured to opposite side portions of end section 17 of the backsheet as illustrated in FIG. 3. Each end section 16 and 17 is provided with an elastic structure described in more detail below. The elastic waist permits the waist portion to expand and fit snugly around the body.

Diaper end sections 16 and 17 are each provided with a sleeves 20 and 21, respectively. Each sleeve 20 or 21 is defined on one side by backsheet 11 and the other side by inner sheet 12 and are bonded together by bonds 22 and 23. Since the elastic sleeves 20 and 21 are similar in structure, like references numerals will be used for corresponding parts and features. Bonds 22 and 23 define lines of point bonds which extend parallel to one another (See FIG. 3). The bonds 22 and 23 close the sides of sleeve 20, leaving the interior open as at 24 (See FIG. 4).

Each sleeve 20 or 21 has mounted therein at least one elastomeric strip 25 and a foam strip 26.

Figure 1:
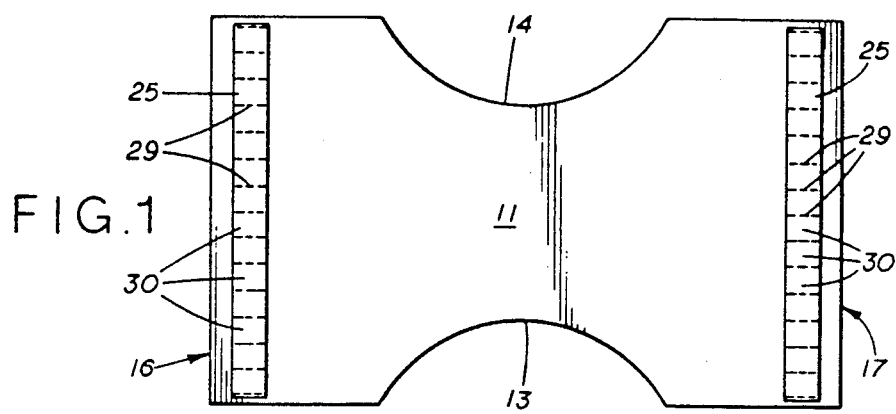
FIGS. 1, 2, and 3 are top plan views of a diaper fabricated according to the present invention, shown in sequence of the fabrication process.

The manner in which the elastomeric and foam strips 25 and 26 are mounted in each sleeve 20 and 21 and the dimensional relationship of these members with respect to their associated sleeve will be described with reference to the sequence FIGS. 1, 2, and 3. As shown in FIG. 1, the backsheet 11 is laid flat and elastomeric strips 25 are placed on each end section 16 and 17 parallel to their outer edges and spaced slightly inwardly from the outer edges to permit bonding.

When using a heat-shrinkable elastomer for strips 25, the length of the strips 25 extend substantially the entire width of the diaper. Each strip 25 is secured to the back sheet 11 at a plurality of longitudinally spaced locations by bonds 29. The bonds 29 form a plurality of heat weld alignments which extend at right angles to the longitudinal axis of the strip 25 (the direction of stretch). Spaces 30 between the bond alignments permit gathering of the nonelastic backsheet 12 upon shrinkage of strip 25 as described in more detail below.

Figure 2:
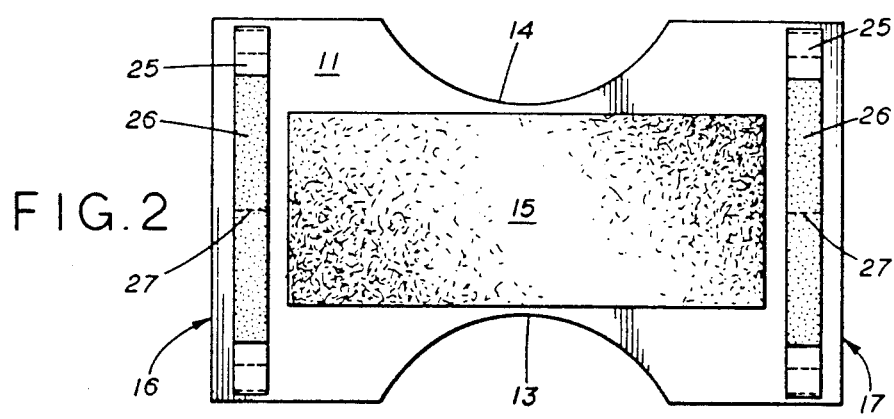

Next, as shown in FIG. 2, a foam strip 26 is placed in overlaying relation to each elastomeric strip 25. Although not critical, each foam strip 26 may have a width substantially the same as its underlying elastomeric strip 25. The length of each foam strip, however, is substantially shorter than the length of its associated elastomeric strip 25 at this stage of the fabrication. Each foam strip 26 is secured to its elastomeric strip 25 at a central portion, usually the midpoint, of the foam strip as shown by weld line 27.

Figure 5:
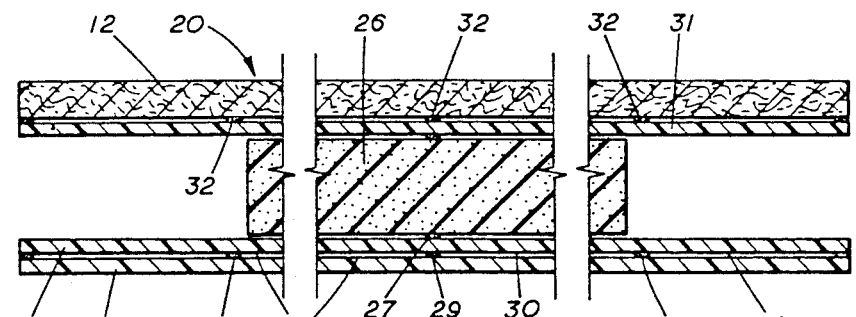
FIG. 5 is a longitudinal cross sectional view of the diaper waist band with the cutting plane taken along 5—5 of FIG. 3.
Figure 6:
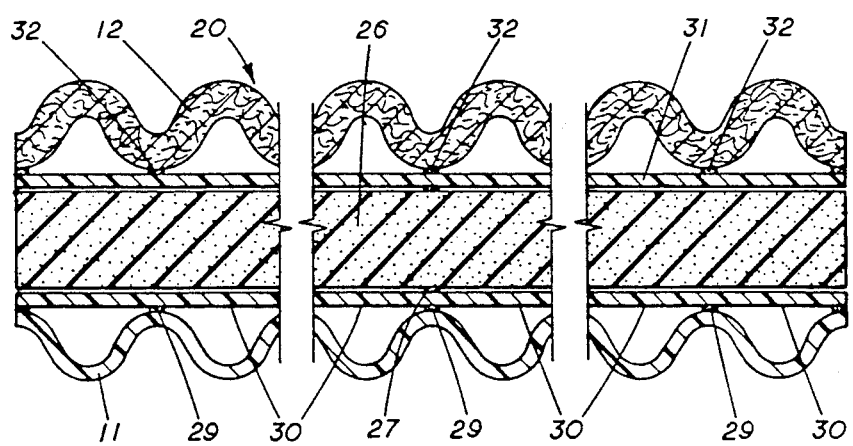
FIG. 6 is a cross sectional of the diaper waist band similar to FIG. 5 with the waist band shown in the contracted position.

Finally, referring to FIG. 3, with the absorbent material 15 in place, the inner sheet 12 is placed in an overlaying relationship to sheet 11 and secured thereto by aligned welds 22 and aligned welds 23 defining sleeve 20 in end section 16 and 21 in end section 17. The cross section interior (space 24) of each sleeve 20 and 21 should be sufficiently large to permit relative movement of the foam strip 26 mounted therein, and the gathering of the sheets 11 and 12 upon contraction of the elastomeric strips 25. The inner sheet 12 may have secured to the underside of each end portion 16 and 17 a second heat shrinkable elastomer strip 31 (shown in FIG. 4). Each strip 31 is aligned with its associated elastomeric strip 25 and is within sleeve, 20 or 21. As shown in FIGS. 5 and 6, strip 31 is secured to sheet 12 at longitudinal spaced intervals by welds 32, thereby permitting sheet 12 to gather in the same manner as sheet 11.

In practice this sequence may be carried out on a continuous film and cut to the proper length following completion of the diaper.

FIGS. 3, 4, and 5 depict the diaper 10 immediately prior to contracting the heat shrinkable elastomeric strips 25. The diaper 10 is placed in an oven and heated to the heat shrink temperature of the thermoelastic. This causes each elastomeric strip 25 (and strip 31 if employed) to contract, pulling with it both the backsheet 11 and the inner sheet 12. The shrinking action of each elastomeric strip 25 causes the backsheet 11 to gather in spaces 30 between bonds 29 of each sleeve 20 and 21 as shown in FIG. 6. Note that each foam strip 26 does not shrink but remains within its associated sleeve 20 and 21. Following cooling of heat shrunk strips 25, the elastomeric members retain their elasticity at room temperature and are stretchable to the FIG. 5 position.

Diaper Materials

The diaper backsheet 11 may be composed of any plastic material presently used for diaper back sheets. These materials are generally water impermeable, but may be air permeable. The common materials used in the diaper backsheet are polyolefins including homopolymers and copolymers of ethylene and propylene. The ethylene copolymers include copolymers of ethylene with $C_3$-$C_8$ olefins (e.g. LLDPE and HDPE), acrylic acid, vinyl acetate and other vinyl esters. The ethylene content generally comprises from 85 to 95 wt %, of the copolymer.

The diaper inner sheet 12 is normally composed of a nonwoven thermoplastic such as nonwoven polypropylene stock. The nonwoven material provides a wicking effect which assist in maintaining dryness.

The elastomeric strips 25 and 31 may be made of any elastic material but preferably are made of heat shrinkable thermoplastic elastomers. The term "thermoplastic elastomers", frequently called rubbery thermoplastics, are blends of a thermoplastic material and elastomer that are processable as a melt, at elevated temperatures, but exhibit properties similar to vulcanized rubber at room temperature. The thermoplastic elastomers are characterized by being shrinkable upon the application of heat. The preferred thermoplastic elastomers are alloys of 10 to 40 wt % of an olefinic elastomer, 50 to 80 wt % of a thermoplastic ethylene copolymer (nonelastomer), and 0 to 12 wt % of processing oil. These components are disclosed in U.S. Pat. No. 4,714,735, the disclosure of which is incorporated herein by reference. Also usable are the heat shrinkable films disclosed in U.S. Pat. No. 4,303,571, the disclosure of which is also incorporated herein by reference. The preferred elastomer component of the heat shrinkable film is a copolymer of ethylene with higher alphaolefin such as ethylene elastomer copolymers including EPM (ASTM D-1418-72a) and DPDM (ethylene-propylene diene elastomer terpolymer, ASTM D-1418-72a.) Specific examples of the preferred elastomer are described in the aforementioned U.S. Pat. Nos. 4,303,571 and 4,714,735.

The preferred thermoplastic ethylene copolymers of the heat shrinkable film include those of ethylene and alphaolefins having 3 to 16 carbon atoms such as propylene or 1-butene. In particular, copolymers of ethylene with vinyl acetate (EVA) or with acrylic acids or methacrylic acids or preferred. The ethylene copolymers generally contain from 50 to 99 wt % ethylene, most preferably from 60 to 95 wt % ethylene. The most preferred ethylene copolymer in the heat shrinkable film is EVA wherein the VA content comprises from 9 to 40 wt %, with about 15 to 35 wt % VA being preferred.

Specific examples of the ethylene copolymer component of the heat shrinkable is disclosed in the aforementioned U.S. Pat. Nos. 4,303,571 and 4,714,735.

The type of process oil includes the liquid hydrocarbon processing extender oils characterized as aromatic, highly aromatic, napthenic and paraffinic oil of medium viscosity range. Oils sold under the trademark Flexon and Sunpar have been found especially useful.

The methods for preparing the heat shrinkable films are disclosed in the aforementioned U.S. Pat. Nos. 4,303,571 and 4.714,735.

The foam strips 26 may be made of polymeric foam such as polyurethane, polyester, polyethylene foams, EVA copolymer foams etc. Many of these foams are commercially available and can be shaped to the strip configuration described herein. Normally the thickness of the foam will be from 2 to 5 mm which when compared to the typical thickness of the elastomeric film and diaper back sheets (typically 0.01 to 0.05 mm each) is substantially thicker. It is preferred that the thickness of the foam strips be from 50% to 150% (preferably between 75% to 125%) of the combined thickness of the other sheets and strips in the diaper waist sleeve as measured normal to the surface sheets 11 and 12. The thickness of the foam strip 26 cushions the stress caused by the stretched elastic strip 25 and provides comfort for the body.

The strips 25 and 31 are relatively narrow, the width preferably representing not more than about 10% but not less than about 3% of the diaper length, so that the elasticity is concentrated in the waist region of the diaper. The length of the foam strips 26 is at least 50%, preferably from about 60% to 80%, of the length of its associated sleeve in its fully extended position. The length of each foam strip 26 is not greater than the length of the sleeve in the contracted position such that foam strip is contained completely within it associated sleeve.

Method of Fabricating the Diaper

The method for fabricating a film or foam composite having a stretchable portion for use in the present invention comprises the steps of:

a) securing to an end portion of a first square or rectangular substantially inelastic thermoplastic film a strip of oriented, heat shrinkable elastomeric film, the film being dimensionally stable, thermally unstable in the stretch oriented condition and contractable to a thermally stable elastic condition by application of heat, and being secured to the inelastic sheet at longitudinally spaced locations;

b) securing a dimensionally stable foam strip to said elastomeric strip, the foam strip overlaying said elastomeric strip having a central portion (e.g. longitudinal midpoint) secured to a central portion (e.g. longitudinal midpoint) of the elastomeric strip and having a length shorter than the length of the elastomeric strip in its oriented, nonshrunk condition;

c) applying a second square or rectangular substantially inelastic film in overlaying relationship to the first film and being secured thereto by two parallel bond rows thereby defining a sleeve which encases the heat shrinkable film and foam strip; and d) applying sufficient heat (in the order of 120° to 150° F) to the elastomeric strip to cause it to contract to its thermally stable and elastic condition with the inelastic sheets gathering in the sleeve area but the foam strip remains substantially stable.

In another embodiment of the method, a second oriented heat shrinkable strip 31 is secured to the underside of the inner sheet 12 as described previously with reference to FIGS. 4–6. The second heat shrinkable strip 31 is also disposed within the sleeve 20 and functions in the same manner as the first heat shrinkable strip 25.

The orientation and heating of the heat shrinkable film strips are described in detail in the aforementioned U.S. Pat. No. 4,714,735. The fabricated diaper 10 has a stretchable waist band. In applying the diaper to the body, the diaper panels are fitted snugly around the body and joined by tabs 18 and 19. This stretches the waist by at least 10% of its contracted length. The foam strips are between the body and the elastomeric strips and cushion stress that is imposed on the body.

Although the present invention have been described with reference to its preferred application (e.g. disposable diapers), it will be appreciated by those skilled in the art that the concepts embodied herein may be applied to other applications such such as garment closures and waist bands. For example, some garments (including diapers) may have only one nonelastic sheet or film, in which case the sleeve in the waist area may be formed by merely overlapping an end portion of the sheet and bonding the overlapped end thereof to the sheet. The overlapped portion forms the sleeve. The elastomeric and foam strips may be secured to the sheet prior to the overlapping step.

What is claimed is:

1. A composite film structure comprising
    (a) a first substantially inelastic film panel
    (b) a second substantially inelastic film panel having an end portion arranged in overlapping relationship with an end portion of the first panel and being secured thereto along parallel and side-by-side bond lines such that the first and second panels between the bond lines define a sleeve;
    (c) an elastomeric strip secured to one of said panels within the sleeve at a plurality of longitudinally spaced bond locations, such that in the stretched position of the elastomeric strip, the panels and the elastomeric strip are substantially flat and parallel, and in the contracted position of the elastomeric strip, the panel gathers between the bond locations; and
    (d) a foam strip mounted in said sleeve and having a central portion secured to a central portion of the elastomeric strip, the sleeve being movable longitudinally outwardly and inwardly from the secured central portion relative to the foam strip, the foam strip being substantially less elastic than the elastomeric strip and having a length at least 50% of the length of the sleeve in the extended position of the elastomeric strip and not greater than the length of the sleeve in the contracted position of the elastomeric strip.

2. The composite film structure of claim 1 wherein the elastomeric strip is composed of a thermoplastic elastomer and said foam strip is composed of polymer foam.

3. The composite film structure of claim 2 wherein the length of the foam strip is 60 to 80% of the length of the sleeve in its extended position.

* * * * *